(12) United States Patent
McKay (10) Patent No.: US 9,283,089 B2
(45) Date of Patent: Mar. 15, 2016

(54) INTERBODY BONE IMPLANT DEVICE (75) Inventor: William F. McKay, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 13/440,241

(22) Filed: Apr. 5, 2012

(65) Prior Publication Data

US 2013/0268075 A1    Oct. 10, 2013

(51) Int. Cl.
*A61F 2/44* (2006.01)
*A61F 2/30* (2006.01)
*A61F 2/28* (2006.01)
*A61F 2/46* (2006.01)

(52) U.S. Cl.
CPC ............... *A61F 2/447* (2013.01); *A61F 2/4465* (2013.01); *A61F 2/30965* (2013.01); *A61F 2002/2817* (2013.01); *A61F 2002/2835* (2013.01); *A61F 2002/30032* (2013.01); *A61F 2002/30034* (2013.01); *A61F 2002/3037* (2013.01); *A61F 2002/3039* (2013.01); *A61F 2002/3052* (2013.01); *A61F 2002/30062* (2013.01); *A61F 2002/3082* (2013.01); *A61F 2002/30383* (2013.01); *A61F 2002/30385* (2013.01); *A61F 2002/30397* (2013.01); *A61F 2002/30448* (2013.01); *A61F 2002/30484* (2013.01); *A61F 2002/30599* (2013.01); *A61F 2002/30607* (2013.01); *A61F 2002/30616* (2013.01); *A61F 2002/30774* (2013.01); *A61F 2002/30823* (2013.01); *A61F 2002/30825* (2013.01); *A61F 2002/4475* (2013.01); *A61F 2002/4655* (2013.01); *A61F 2310/00017* (2013.01); *A61F 2310/00023* (2013.01); *A61F 2310/00029* (2013.01); *A61F 2310/00047* (2013.01); *A61F 2310/0097* (2013.01); *A61F 2310/00179* (2013.01); *A61F 2310/00239* (2013.01); *A61F 2310/00317* (2013.01); *A61F 2310/00359* (2013.01); *A61F 2310/00365* (2013.01)

(58) Field of Classification Search
CPC .............. A61F 2002/30062; A61F 2210/0004; A61F 2220/0025; A61F 2/4455; A61F 2002/30387–2002/30388; A61F 2002/30383; A61F 2002/3052; A61F 2002/30385; A61F 2002/30359; A61F 2002/30975; A61F 2/44; A61F 2/447
USPC ............................................ 623/17.11–17.16
See application file for complete search history.

(56) References Cited

U.S. PATENT DOCUMENTS

| | | | |
|---|---|---|---|
| 4,137,919 A * | 2/1979 | Farin et al. ...................... | 606/51 |
| 5,531,791 A | 7/1996 | Wolfinbarger, Jr. | |
| 5,865,848 A * | 2/1999 | Baker ................... | A61F 2/4455 606/247 |
| 6,520,993 B2 * | 2/2003 | James et al. ............... | 623/17.16 |

(Continued)

*Primary Examiner* — Jacqueline Johanas
(74) *Attorney, Agent, or Firm* — Sorell Lenna & Schmidt LLP (57) ABSTRACT

An expandable implant device for implantation at a surgical site is provided. The implant device is made of cortical bone and includes a top and bottom piece, both pieces configured to couple with each other. The top piece has superior and inferior surfaces, and at least a tapered leading end configured to distract open an intervertebral disc space so that the top piece can be slidably inserted over the bottom piece until a desired overlap is achieved. A composite interbody bone implant device is also provided including a body skeleton having a non-bone composition, such as a polymer, formed into a shape and including one or more cavities which can be filled with other material, for example, allograft material. A method of placing an expandable device into a disc space is also provided.

15 Claims, 2 Drawing Sheets

(56) References Cited

U.S. PATENT DOCUMENTS

| | | |
|---|---|---|
| 7,498,041 B2 | 3/2009 | Masinaei et al. |
| 7,815,682 B1 | 10/2010 | Peterson et al. |
| 8,900,307 B2* | 12/2014 | Hawkins ............... A61F 2/4455 623/17.16 |
| 2002/0120338 A1 | 8/2002 | Boyer, II et al. |
| 2003/0009235 A1 | 1/2003 | Manrique et al. |
| 2003/0114936 A1 | 6/2003 | Sherwood et al. |
| 2003/0135275 A1* | 7/2003 | Garcia ............... A61B 17/1671 623/17.11 |
| 2003/0167092 A1 | 9/2003 | Foley |
| 2004/0087969 A1* | 5/2004 | Kayan et al. ................... 606/110 |
| 2004/0230308 A1* | 11/2004 | Michelson ................. 623/17.11 |
| 2005/0021142 A1 | 1/2005 | Ganz et al. |
| 2005/0085922 A1 | 4/2005 | Shappley et al. |
| 2005/0125062 A1* | 6/2005 | Biedermann et al. ...... 623/17.11 |
| 2006/0058876 A1* | 3/2006 | McKinley ............. A61F 2/4611 623/17.11 |
| 2006/0058880 A1* | 3/2006 | Wysocki et al. ............ 623/17.15 |
| 2006/0122702 A1* | 6/2006 | Michelson ................. 623/17.11 |
| 2006/0233851 A1 | 10/2006 | Simon et al. |
| 2006/0235519 A1* | 10/2006 | Michelson ................. 623/17.11 |
| 2006/0280803 A1 | 12/2006 | Kumar et al. |
| 2006/0293757 A1 | 12/2006 | McKay et al. |
| 2007/0088437 A1* | 4/2007 | Betz et al. .................. 623/17.11 |
| 2007/0098756 A1 | 5/2007 | Behnam |
| 2007/0233272 A1* | 10/2007 | Boyce et al. ................ 623/23.63 |
| 2007/0299441 A1* | 12/2007 | Hoffman et al. ................. 606/61 |
| 2008/0033440 A1* | 2/2008 | Moskowitz ........ A61B 17/0642 606/251 |
| 2008/0091270 A1* | 4/2008 | Miller et al. ................ 623/17.16 |
| 2008/0114465 A1 | 5/2008 | Zanella et al. |
| 2008/0249622 A1* | 10/2008 | Gray ..................... A61F 2/4455 606/86 A |
| 2008/0281431 A1 | 11/2008 | Missos |
| 2009/0005870 A1* | 1/2009 | Hawkins et al. ........... 623/17.11 |
| 2009/0099661 A1* | 4/2009 | Bhattacharya et al. .... 623/17.16 |
| 2009/0130173 A1* | 5/2009 | Behnam et al. ................ 424/426 |
| 2009/0155378 A1 | 6/2009 | Behnam et al. |
| 2009/0192474 A1 | 7/2009 | Wei et al. |
| 2009/0254182 A1* | 10/2009 | Kovarik et al. ............ 623/17.11 |
| 2009/0319045 A1 | 12/2009 | Truncale et al. |
| 2010/0030333 A1* | 2/2010 | Michelson ................. 623/17.11 |
| 2010/0042216 A1 | 2/2010 | Kilpela et al. |
| 2010/0161056 A1* | 6/2010 | Voellmicke et al. ....... 623/17.11 |
| 2010/0268232 A1 | 10/2010 | Betz et al. |
| 2010/0286783 A1 | 11/2010 | Lechmann et al. |
| 2010/0292739 A1* | 11/2010 | Schwab ........................ 606/305 |
| 2011/0144766 A1 | 6/2011 | Kale et al. |
| 2012/0004729 A1* | 1/2012 | Zipnick ..................... 623/17.16 |
| 2012/0330425 A1* | 12/2012 | Zipnick ..................... 623/17.16 |
| 2013/0073046 A1* | 3/2013 | Zaveloff et al. ............ 623/17.16 |
| 2013/0190876 A1* | 7/2013 | Drochner et al. .......... 623/17.16 |
| 2014/0121777 A1* | 5/2014 | Rosen et al. ............... 623/17.16 |

\* cited by examiner

INTERBODY BONE IMPLANT DEVICE

BACKGROUND

Chronic back problems cause pain and disability for a large segment of the population. In many cases, chronic back problems are caused by intervertebral disc disease. When an intervertebral disc is diseased, the vertebrae between which the disc is positioned may be inadequately supported, resulting in persistent pain. Stabilization and/or arthrodesis of the intervertebral joint can reduce the pain and debilitating effects associated with disc disease.

Spinal stabilization systems and procedures have been developed to stabilize diseased intervertebral joints and, in some cases, to fuse the vertebrae that are adjacent to the diseased joint space. Most fusion techniques include removing some or all of the disc material from the affected joint, and stabilizing the joint by inserting an implant, for example, a bone graft or other material to facilitate fusion of the vertebrae, in the cleaned intervertebral space.

The use of bone grafts and bone substitute materials in orthopedic medicine is known. Conventionally, bone tissue regeneration is achieved by filling a bone repair site with a bone graft. Over time, the bone graft is incorporated by the host and new bone remodels the bone graft. In order to place the bone graft, it is common to use a monolithic bone graft or to form an osteoimplant comprising particulated bone in a carrier. The carrier is thus chosen to be biocompatible, to be resorbable, and to have release characteristics such that the bone graft is accessible. The natural cellular healing and remodeling mechanisms of the body coordinate removal of bone and bone grafts by osteoclast cells and formation of bone by osteoblast cells.

In the spinal surgery field, surgical procedures are often performed to correct problems with displaced, damaged or degenerated intervertebral discs due to trauma, disease or aging. Bone graft materials are often used in spine fusion surgery. Current spinal fusion implants utilize grafts of either bone or artificial implants to fill the intervertebral disc space.

In particular, one method of treating a damaged disc is by immobilizing the area around the injured portion and fusing the immobilized portion by promoting bone growth between the immobilized spine portions. This often requires implantation of an intervertebral device to provide the desired spacing between adjacent vertebrae to maintain foraminal height and decompression. That is, an intervertebral implant comprising an interbody fusion device may be inserted into the intervertebral disc space of two neighboring vertebral bodies or into the space created by removal of damaged portions of the spine.

In some instances, a formed implant, whether monolithic or particulated and in a carrier, is substantially solid at the time of implantation and thus does not conform to the implant site. Further, most implants are substantially formed at the time of implantation in limited sizes and shapes and provide little ability for customization.

While generally effective, the use of bone grafts has some limitations. Autologous bone grafts, being obtained from the patient, require additional surgery and present increased risks associated with its harvesting, such as risk of infection, blood loss and compromised structural integrity at the donor site. Bone grafts using cortical bone remodel slowly because of their limited porosity. Traditional bone substitute materials and bone chips are more quickly remodeled but cannot immediately provide mechanical support. In addition, while bone substitute materials and bone chips can be used to fill oddly shaped bone defects, such materials are not as well suited for wrapping or resurfacing bone. Indeed, the use of bone grafts is generally limited by the available shapes and sizes of grafts provided.

With regards to bone grafts, allograft bone is a reasonable bone graft substitute for autologous bone. It is readily available from cadavers and avoids the surgical complications and patient morbidity associated with harvesting autologous bone. Allograft bone is essentially a load-bearing matrix comprising cross-linked collagen, hydroxyapatite, and osteoinductive bone morphogenetic proteins. Human allograft tissue is widely used in orthopaedic surgery.

Indeed, an allograft implant is a preferred material by surgeons for conducting interbody fusions because it will remodel over time into host bone within the fusion mass. However, though allograft tissue has certain advantages over the other treatments, allograft implants are typically available in limited size ranges, thus making it difficult to provide implants, in particular, interbody implants in a preferred geometrical shape. Indeed, allograft implants may only provide temporary support, as it is difficult to manufacture the allograft with a consistent shape and strength. On the other hand, synthetic polymer implants such as poly-ether-etherketone (PEEK) can be manufactured into any geometrical shape. However, synthetic polymer implants, unlike allograft implants, have some strength limitations and will not remodel into host bone over time like an allograft implant. Synthetic polymer implants also do not allow for direct bone attachment or bonding to further stabilize the implant and fusion mass. In addition, surgical procedures are increasingly moving towards minimally invasive surgical procedures in which smaller interbody cages can be inserted through smaller surgical incisions and expanded once placed in the disc space. Because of the allograft size limitations, current expandable interbody cages are generally manufactured from metal and plastic materials.

Therefore, it would be desirable to construct an implant, particularly an interbody implant, that has components that allow remodeling and disc distraction.

SUMMARY

The present disclosure fills the need by providing devices (for example, medical devices), systems and methods for enhancing the utility of allograft tissue as an interbody fusion material. In particular, the present disclosure provides an expandable implant device for implantation at a surgical site. The implant device is prepared of cortical bone and has a top and bottom piece. The bottom piece of the implant device has superior and inferior surfaces and is configured to couple with the top piece. The top piece also has superior and inferior surfaces, a leading end and a trailing end. The leading end, in some embodiments, of the top piece is tapered or narrower in size and is configured to distract open an intervertebral disc space so that the top piece can be slidably inserted over the bottom piece until a desired overlap is achieved.

In another aspect, the superior surface of the bottom piece and the inferior surface of the top piece, each comprise a mechanical feature configured to interlock the top piece with the bottom piece. In various aspects, the mechanical feature comprises a recess, projection, rib, groove or a combination thereof. The superior surface of the bottom piece and the inferior surface of the top piece are configured to slide over one another.

In certain embodiments, the top and bottom pieces of the expandable implant device can have many shapes including circular, oblong, oval, curved, triangular, other polygonal or non-polygonal shapes. In other embodiments, the tapered leading end of the top piece has a shape that is bullet, round, oval, curved or triangular in shape.

In various other embodiments, the present disclosure provides an expandable implant device comprising a composite of allograft bone tissue and a non-bone composition such as a polymer composition, for example, poly-ether-ether-ketone (PEEK) and/or other polymer compositions. According to some embodiments, a composite bone implant device is provided which utilizes and retains allograft pieces within a polymer structure. This advantageously enables the beneficial properties of allograft tissue and the beneficial attributes of polymers to be fully realized. For example, the remodeling capability of allograft tissue is advantageously combined with the polymer's ability to enable implants to be formed into any geometrical shape or size.

In some embodiments, the composite implant is configured to increase the surface area contact of the allograft with the host bone, which will result in faster fusion and incorporation of the composite implant into host bone that allows a stronger fusion mass. In some embodiments, the allograft bone used in the implant is surface demineralization to increase its osteoinductivity and fusion with the host bone. In some embodiments, the implant optimizes the non-bone and bone content of the implant body such that the majority of the mechanical load is carried by the allograft, while the non-bone material holds the allograft pieces together. In some embodiments, the portion of the allograft that is not demineralized comprises load bearing and/or higher compressive strength allograft material.

According to one aspect, an implant device is provided comprising a body, which comprises a skeleton of non-bone composition formed into a shape and including at least one cavity. The implant device also comprises a biocompatible material provided within the at least one cavity of the body skeleton, wherein the body skeleton is formable into a shape and size adapted for implantation at a surgical site.

In various embodiments, the implant device having a skeleton body and at least one cavity therein comprises a top piece and a bottom piece. The bottom piece of the implant device has superior and inferior surfaces and is configured to couple with the top piece. The top piece has superior and inferior surfaces, a leading end and a trailing end. The leading end of the top piece is tapered or narrower than the trailing end and is configured to distract open an intervertebral disc space so that the top piece can be slidably inserted over the bottom piece until a desired overlap is achieved. Both the top and bottom pieces are prepared of non-bone material to provide a polymeric skeleton which contains at least one cavity. The non-bone composition includes at least one of a polymer, ceramic, metal or combinations thereof. In several aspects, the skeleton comprises poly-ether-ether-ketone (PEEK), poly-ether-ketone-ketone (PEKK), or a combination thereof.

In various embodiments, a biocompatible material is provided within the at least one cavity of the bottom piece or the top piece or both. The biocompatible material can comprise an osteoinductive material. The osteoinductive material comprises at least one of autologous bone, bone allograft, bone xenograft or a non-bone implant.

In various embodiments, the superior surface of the bottom piece and the inferior surface of the top piece of the composite implant device comprise a mechanical feature configured to interlock the bottom piece with the top piece. The mechanical feature comprises a recess, projection, rib, groove or a combination thereof.

This disclosure also provides a method of placing an expandable implant device into a disc space. The method includes the steps of inserting a bottom piece of the implant device into a disc space and holding the bottom piece stationary with an insertion instrument; inserting a top piece with a ratcheting instrument, the top piece having superior and inferior surfaces, a tapered leading end and a trailing end, the leading tapered end of the top piece configured to distract open an intervertebral disc space for slidably inserting the top piece over the bottom piece. In some embodiments, the top piece and the bottom piece comprise cortical bone. In other embodiments the top piece and the bottom piece comprise non-bone composition including at least one cavity. In other embodiments, the superior surface of the bottom piece and the inferior surface of the top piece comprise a mechanical feature configured to interlock the top piece over the bottom piece. In several aspects, the at least one cavity in the top piece, the bottom piece or both is provided with biocompatible material.

According to another aspect, a composite interbody bone implant device is provided comprising a body, which comprises a non-bone composition formed into a shape and including a plurality of cavities and an osteoinductive material provided within the cavities of the body, wherein the body is formable into a shape and size adapted for implantation at a surgical site.

While multiple embodiments are disclosed, still other embodiments of the present disclosure will become apparent to those skilled in the art from the following detailed description, which is to be read in connection with the accompanying drawing(s). As will be apparent, the disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE DRAWINGS

In part, other aspects, features, benefits and advantages of the embodiments will be apparent with regard to the following description, appended claims and accompanying drawing(s) where:

DETAILED DESCRIPTION

Definitions

To aid in the understanding of the disclosure, the following non-limiting definitions are provided:

"Bioactive agent or bioactive compound," as used herein, refers to a compound or entity that alters, inhibits, activates, or otherwise affects biological or chemical events. For example, bioactive agents may include, but are not limited to, osteogenic or chondrogenic proteins or peptides, anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anticholinergics, anti-glaucoma compounds, anti-parasite and/or anti-protozoal compounds, modulators of cell-extracellular matrix interactions including cell growth inhibitors and anti-adhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. In some embodiments, the bioactive agent is a growth factor, cytokine, extracellular matrix molecule or a fragment or derivative thereof, for example, a cell attachment sequence such as RGD.

"Biocompatible," as used herein, refers to materials that, upon administration in vivo, do not induce undesirable long-term effects.

"Bone," as used herein, refers to bone that is cortical, cancellous or cortico-cancellous of autogenous, allogenic, xenogenic, or transgenic origin.

"Demineralized," as used herein, refers to any material generated by removing mineral material from tissue, for example, bone tissue. In certain embodiments, the demineralized compositions described herein include preparations containing less than 5% calcium and, in some embodiments, less than 1% calcium by weight. Partially demineralized bone (for example, preparations with greater than 5% calcium by weight but containing less than 100% of the original starting amount of calcium) is also considered within the scope of the disclosure. In some embodiments, demineralized bone has less than 95% of its original mineral content. Demineralized is intended to encompass such expressions as "substantially demineralized," "partially demineralized," and "fully demineralized."

"Demineralized bone matrix" or "DBM" as used herein, refers to any material generated by removing mineral material from bone tissue. In some embodiments, the DBM compositions as used herein include preparations containing less than 5% calcium and, in some embodiments, less than 1% calcium by weight. Partially demineralized bone (for example, preparations with greater than 5% calcium by weight but containing less than 100% of the original starting amount of calcium) are also considered within the scope of the disclosure.

"Osteoconductive," as used herein, refers to the ability of a non-osteoinductive substance to serve as a suitable template or substance along which bone may grow.

"Osteogenic," as used herein, refers to the ability of an agent, material, or implant to enhance or accelerate the growth of new bone tissue by one or more mechanisms such as osteogenesis, osteoconduction, and/or osteoinduction.

"Osteoimplant," as used herein, refers to any bone-derived implant prepared in accordance with the embodiments of this disclosure and therefore is intended to include expressions such as bone membrane or bone graft.

"Osteoinductive," as used herein, refers to the quality of being able to recruit cells from the host that have the potential to stimulate new bone formation. Any material that can induce the formation of ectopic bone in the soft tissue of an animal is considered osteoinductive.

"Superficially demineralized," as used herein, refers to bone-derived elements possessing at least about 90 weight percent of their original inorganic mineral content, the expression "partially demineralized" as used herein refers to bone-derived elements possessing from about 8 to about 90 weight percent of their original inorganic mineral content and the expression "fully demineralized" as used herein refers to bone containing less than 8% of its original mineral context.

The term "allograft" refers to a graft of tissue obtained from a donor of the same species as, but with a different genetic make-up from, the recipient, as a tissue transplant between two humans.

The term "autologous" refers to being derived or transferred from the same individual's body, such as for example an autologous bone marrow transplant.

The term "implantable" as utilized herein refers to a biocompatible device retaining potential for successful surgical placement within a mammal.

The expression "implantable device" and expressions of like import as utilized herein refers to any object implantable through surgical, injection, or other suitable means whose primary function is achieved either through its physical presence or mechanical properties.

The term "morbidity" refers to the frequency of the appearance of complications following a surgical procedure or other treatment.

The term "osteoinduction" refers to the ability to stimulate the proliferation and differentiation of pluripotent mesenchymal stem cells (MSCs). In endochondral bone formation, stem cells differentiate into chondroblasts and chondrocytes, laying down a cartilaginous ECM, which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype.

The term "osteoconduction" refers to the ability to stimulate the attachment, migration, and distribution of vascular and osteogenic cells within the graft material. The physical characteristics that affect the graft's osteoconductive activity include porosity, pore size, and three-dimensional architecture. In addition, direct biochemical interactions between matrix proteins and cell surface receptors play a major role in the host's response to the graft material.

The term "osteogenic" refers to the ability of a graft material to produce bone independently. To have direct osteogenic activity, the graft must contain cellular components that directly induce bone formation. For example, a collagen matrix seeded with activated MSCs would have the potential to induce bone formation directly, without recruitment and activation of host MSC populations. Because many osteoconductive scaffolds also have the ability to bind and deliver bioactive molecules, their osteoinductive potential will be greatly enhanced.

The term "patient" refers to a biological system to which a treatment can be administered. A biological system can include, for example, an individual cell, a set of cells (for example, a cell culture), an organ, or a tissue. Additionally, the term "patient" can refer to animals, including, without limitation, humans.

The term "treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols, which have only a marginal effect on the patient.

The term "xenograft" refers to tissue or organs from an individual of one species transplanted into or grafted onto an organism of another species, genus, or family.

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Certain terminology, which may be used in the following description is for convenience only and is not limiting. For example, the words "right", "left", "top" and "bottom" designate directions in the drawings to which reference is made. The words, "anterior", "posterior", "superior", "inferior", "lateral" and related words and/or phrases designate preferred positions and orientations in the human body to which reference is made and are not meant to be limiting. The terminology includes the above-listed words, derivatives thereof and words of similar import.

Expandable Implant Devices

Bone allograft is a preferred material by surgeons for conducting interbody fusions because it will remodel over time into host bone within the fusion mass, but a limitation with the allograft is that it is only available in limited size ranges making it difficult to provide interbody implants in a preferred geometrical shape. On the other hand, synthetic polymers such as poly-ether-ether-ketone (PEEK) can be manufactured into any geometrical shape, but have some strength limitations and are a permanent implant that will not remodel into host bone over time like an allograft. Polymer compositions also do not allow for direct bone attachment or bonding to further stabilize the implant and fusion mass. In addition, surgical procedures are increasingly moving towards minimally invasive surgical procedures in which smaller interbody cages can be inserted through smaller surgical incisions and expanded once placed in the disc space. Because of the allograft size limitations, current expandable interbody cages are manufacture from metal and plastic materials.

The present disclosure overcomes the drawbacks of the prior art by providing various exemplary designs of bone implants comprising desirable remodelable allograft composition and disc distraction properties. The present disclosure also provides implants containing non-bone skeleton structures configured to include cavities including other materials, for example, allograft material.

In some embodiments, the composite implant is configured to increase the surface area contact of the allograft with the host bone, which will result in faster fusion and incorporation of the composite implant into host bone that allows a stronger fusion mass. In some embodiments, the allograft bone used in the implant is surface demineralization to increase its osteoinductivity and fusion with the host bone. In some embodiments, the implant optimizes the non-bone and bone content of the implant body such that the majority of the mechanical load is carried by the allograft, while the non-bone material holds the allograft pieces together. In some embodiments, the portion of the allograft that is not demineralized comprises load bearing and/or higher compressive strength allograft material.

Various exemplary configurations according to the present disclosure involve providing cortical allograft constructs that mechanically interlock together and slide over each other to distract open the intervertebral disc space as they are inserted to form a single interbody implant. Advantageously, it is noted that an implant device may be provided in any configuration, size and shape, as per the requirements of the desired target site. Thus, almost unlimited ranges of sizes and shapes of optimized bone implant devices may be provided. In one example, an implant device may be configured to be adapted for use as an interbody fusion device, for example, in spinal fusion procedures. However, alternate configurations of the implant device may be contemplated to suit the needs of a patient's bone graft target site.

Figure 1:
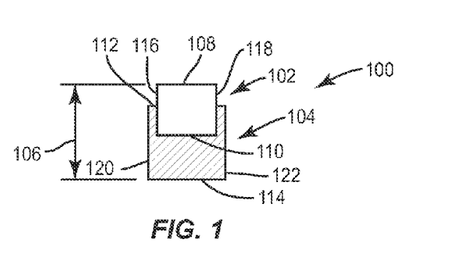
FIG. 1 is a front sectional view of an exemplary expandable bone implant according to one embodiment.

FIG. 1 depicts a representative expandable bone implant 100 prepared from cortical allograft. Implant 100 comprises, consists essentially of or consists of two elements, a top piece 102 and a bottom piece 104. Each piece has a superior and an inferior surface. Accordingly, top piece 102 has a superior surface 108 and an inferior surface 110. Similarly, the bottom piece 104 has a superior surface 112 and an inferior surface 114. Each superior and inferior surfaces are joined by surfaces forming a leading end and a trailing end. Accordingly, top piece 102 has a leading end 116 and a trailing end 118 and bottom piece 104 has a leading end 120 and a trailing end 122. The bottom allograft piece 104 has a mechanical feature (not shown in FIG. 1), for example a rib, groove, recess, and/or projection that can interlock with the top allograft piece 102.

The bottom allograft piece 104 can be inserted first in disc space 106. Leading end 116 of top allograft piece 102 is tapered or narrower than trailing end 118 so that top piece 102 can distract open disc space 106 and slide over the bottom allograft piece 104 until the two pieces lock into place. An insertion tool can be used to hold the bottom piece 104 in place as the top piece 102 is pushed slidingly over bottom piece 104 utilizing, for example, a ratcheting mechanism. The inferior surface of the top piece slidably engages the superior surface of the bottom piece. One or more surfaces of the top and/or bottom piece may comprise a lubricant to reduce friction and ease insertion.

In some embodiments, the implant device contacts host bone and the implant device comprises non-bone material, the contact surface area of the non-bone material and the cortical bone to the host bone comprises from about 5% to about 50% or from about 10% to about 20% of the implant. In some embodiments, the implant device comprises non-bone material and the non-bone material comprises from about 10 wt. % to about 60 wt. % of the implant. In some embodiments, the implant device comprises bone material and the bone material comprises from about 40 wt. % to about 90 wt. % of the implant. In some embodiments, the implant device comprises bone material and the bone material comprises from about 10 wt. % to about 60 wt. % of the implant.

Figure 2:
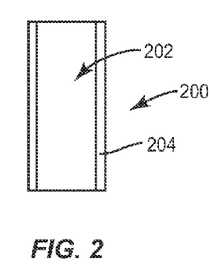
FIG. 2 is a top view of a straight shaped expandable implant according to another embodiment.
Figure 3:
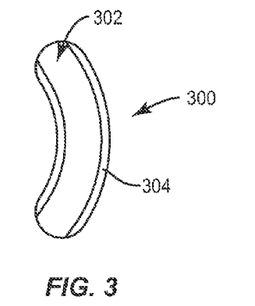
FIG. 3 is top view of an expandable curved shaped bone implant device according to an alternate embodiment.

FIG. 2 illustrates another embodiment of the expandable bone implant 200 having a straight shape, while FIG. 3 illustrates another embodiment wherein the expandable bone implant 300 has a curved shape depending upon the desired form best suited for a selected surgical procedure. Bone implant device 200 comprises a top piece 202 and a bottom piece 204 configured to lock one on top of the other. Similarly, bone implant device 300 comprises a top piece 302 and a bottom piece 304 configured to lock one on top of the other. The implant is expandable as the bottom piece is expanded by the depth, width and height of the top piece. In some embodiments, the polymer and/or allograft material will also expand as it contacts bodily fluid after implantation at the target tissue site.

Figure 4:
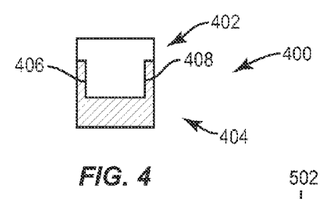
FIG. 4 is a front sectional view of an exemplary expandable bone implant device according to another embodiment.

FIG. 4 illustrates a front sectional view of another embodiment of an expandable bone implant 400 prepared from cortical allograft and comprising, consisting essentially of or consisting of two elements, a top piece 402 and a bottom piece 404. Top piece 402 has leading end 406 and trailing end 408, the leading end 406 is tapered in a bullet nose configuration as shown in FIG. 5.

Figure 5:
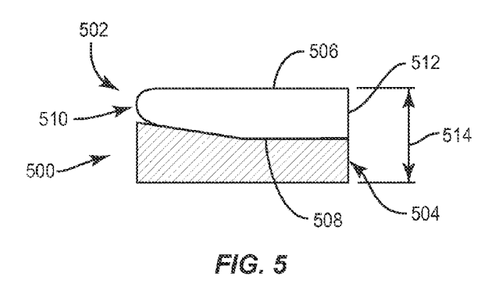
FIG. 5 is a cross sectional view through the center of the expandable bone implant illustrated in FIG. 4.

FIG. 5 is a cross section view of the implant device 500 taken through the center of the implant device shown in FIG. 4. Top piece 502 has a superior surface 506 and an inferior surface 508, a leading end 510 and a trailing end 512. Leading end 510 has the tapered configuration of a bullet nose enabling top piece 502 to distract open disc space 514 to slide over the bottom piece 504 until the two pieces lock into place.

Figure 6:
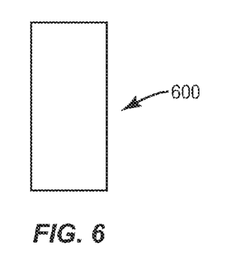
FIG. 6 is a top view of the expandable bone implant illustrated in FIG. 4.
Figure 7:
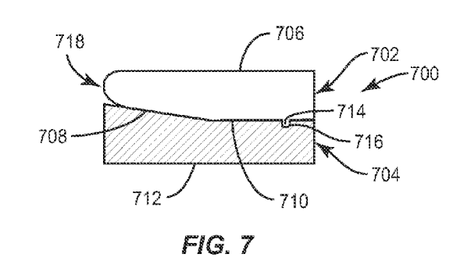
FIG. 7 is a side view of another exemplary expandable bone implant in accordance with principles of this disclosure.

FIG. 6 is a top view of an expandable bone implant 600 as illustrated in FIG. 4. In yet another embodiment illustrated in FIG. 7, expandable bone implant 700 comprises, consists essentially of or consists of a top piece 702 and a bottom piece 704, both manufactured from cortical allograft. Top piece 702 has superior and inferior surfaces 706 and 708 and bottom piece 704 has superior and inferior surfaces 710 and 712. Inferior surface 708 of top piece 702 includes at least one projection or rib 714 while superior surface 710 of bottom piece 704 has a recess or groove 716. Projection or rib 714 locks with recess or groove 716 as top piece 702 slides over bottom piece 704 with the help of, in some embodiments, a ratcheting inserter. The recess and/or projection, in some embodiments, can be mating and include, for example, corresponding voids, apertures, bores, depressions, holes, indentations, grooves, channels, notches or the like, which can mate with each other. Like top piece 502 illustrated in FIG. 5, top piece 702 has a tapered leading end 718 enabling top piece 702 to distract the disc space open before sliding over the bottom piece 704 until projection 714 locks into recess 716.

Figure 8:
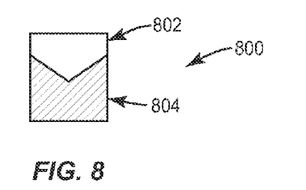
FIG. 8 is a front sectional view of another exemplary expandable bone implant device in accordance with the principles of this disclosure.

FIG. 8 is a front sectional view of yet another embodiment of the expandable allograft bone implant 800 having a top piece 802 that is triangularly shaped to mate with a bottom piece 804.

Figures 9, 10:
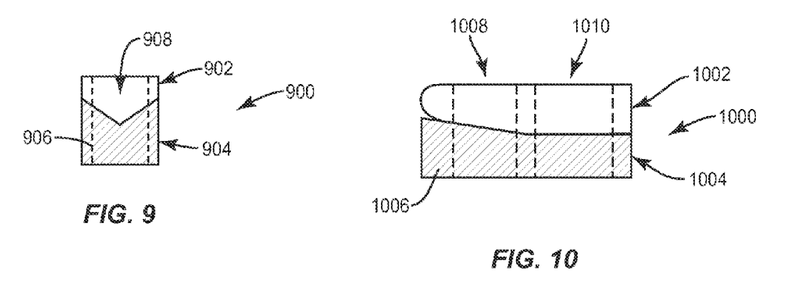
FIG. 9 is a front sectional view of an exemplary expandable bone implant according to an another embodiment.
FIG. 10 is a side view of another exemplary expandable bone implant in accordance with principles of this disclosure.

FIG. 9 illustrates a front sectional view of another embodiment of an expandable implant device 900. In this embodiment, both the top piece 902 and the bottom piece 904 comprise a polymer skeleton 906, for example, PEEK, and at least one cavity 908 that can be packed with cortical allograft inserts. Advantageously, the incorporation of PEEK skeletons for the top and bottom pieces of the expandable implant allows for the incorporation of design features that enable a better mechanical lock of the top and bottom pieces and adaptation to insertion instruments.

FIG. 10 is a side view of another embodiment of an expandable implant 1000 wherein the top and bottom pieces 1002, 1004 have a polymer skeleton 1006 having two cavities 1008, 1010 that can be filled with allograft as indicated in phantom by interrupted lines.

Figure 11:
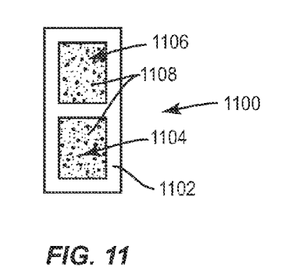
FIG. 11 depicts a top view of an exemplary implant device inserted within an intervertebral disc space in accordance with principles of this disclosure.

FIG. 11 is a top view of an expandable implant 1100 according to one embodiment. Implant 1100 may comprise a body skeleton 1102 which may comprise, a 'skeleton' structure configured to include at least one window or cavity within which a substance 1108, such as an allograft material may be inserted and retained. The term 'cavity' includes and encompasses voids, apertures, bores, depressions, holes, indentations, grooves, channels, notches or the like. In some embodiments the skeleton comprises a plurality of cavities. As illustrated in FIG. 11, body skeleton 1102 includes two cavities 1104, 1106 which may be provided throughout one or more surfaces of and/or within the body skeleton 1102, thus enabling a plurality of allograft pieces to be retained by the body 1102 in various locations.

The body 1102 may comprise any non-bone composition, in particular, any biocompatible material including but not limited to a metal, such as, for example, cobalt-chromium-molybdenum (CCM) alloys, titanium, titanium alloys, stainless steel, aluminum, a ceramic such as, for example, zirconium oxide, silicon nitride, an allograft, an autograft, a metal-allograft composite, a polymer such as, for example, polyaryl ether ketone (PAEK), polyether ether ketone (PEEK), polyether ketone ketone (PEKK), polyetherketone (PEK), polyetherketone ether-ketone-ketone (PEK-EKK) or a combination thereof. The polymers may be reinforced with a fiber such as, for example, a carbon fiber or other thin, stiff fiber.

Advantageously, the body 1102 may be formed, for example, via injection molding and/or machining into any size or shape to accommodate the desired application and/or delivery conditions. The body 1102 may further be configured to include any desired features, such as cavities, projections, in any desired location or orientation, as discussed further below.

In various embodiments, the delivery of the expandable implant device and its component pieces can be facilitated by using a lubricant to lubricate the implant device and its components prior to insertion into an intervertebral disc space. Suitable lubricants include without limitation mineral oils, bodily fluids, fat, saline or hydrogel coatings. Other useful lubricants include hyaluronic acid, hyaluronan, lubricin, polyethylene glycol and combinations thereof.

The body of all expandable implants according to principles of this disclosure may also include a mechanism or feature for engaging an implant insertion instrument. The mechanism or feature for engaging the insertion instrument may take on any form including, for example, one or more bores for receiving one or more projections formed on the implant insertion instrument, one or more projections for engaging one or more bores formed on the implant insertion instrument, one or more channels for receiving one or more tips formed on the implant insertion instrument, one or more threaded bores for receiving one or more threaded shafts or screws.

The body of the expandable implants described herein may also include a mechanism or features for reducing and/or preventing slippage or migration of the implant device 1100 during insertion. For example, one or more surfaces of the body 1102 may include projections such as ridges or teeth for increasing the friction between the device 1100 and the adjacent contacting surfaces of the vertebral bodies so to prevent movement of the implant device 1100 after introduction to a desired disc space.

In some embodiments, the surfaces of the body 1102 include at least one cavity 1104 or a plurality of cavities 1104, 1106. Each cavity 1104, 1106 may be provided in any of a variety of shapes in addition to the generally rectangular shape shown in FIG. 11, including but not limited to generally circular, oblong, curved, triangular and other polygonal or non-polygonal shapes. The same or different types of cavity shapes and sizes may be provided in each body 1102. Each cavity 1104, 1106 may be formed to pass entirely through the body 1102 for promoting fusion between the upper and lower vertebral bodies so as to allow a boney bridge to form through the implant device 1100. Alternately, cavities 1104, 1106 may be formed to partially pass through the body 1102, or may be formed only on one or more surfaces thereof.

In addition to the body of the expandable implant being enabled to be provided in various configurations, shapes and sizes, the body may include any number of cavities in different arrangements, locations, sizes and shapes. For example, the arrangement and location of cavities may be determined based on application of the implant device.

According to some embodiments, fusion may be facilitated or augmented by introducing or positioning various osteoinductive and/or osteogenic materials within the cavities in the implant device. Such osteoinductive materials may be introduced before, during, or after insertion of the exemplary implant device, and may include (but are not necessarily limited to) autologous bone harvested from the patient receiving the implant device, bone allograft, bone xenograft, any number of non-bone implants (for example ceramic, metallic, polymer), bone morphogenic protein, and/or bio-resorbable compositions. The osteogenic material may be selected from among many known to those skilled in the art. For example, the osteogenic material may comprise minerals such as calcium phosphate or calcium sulfate minerals, bone, including xenograft, allograft or autograft bone, or the like. The osteogenic material may also comprise demineralized bone matrix (DBM), osteoinductive factors such as bone morphogenetic proteins (for example human BMP-2 or human BMP-7 or heterodimers thereof) whether recombinantly produced or purified from tissues, LIM mineralization proteins (LMPs), or the like. The osteogenic material may also comprise a binder material such as blood, clottable blood fractions, platelet gel, collagen, gelatin, carboxymethyl cellulose, or other similar materials that will serve to bind together harder particles or materials such as mineral particles (for example bone or synthetic mineral particles) so as to create a three-dimensionally stable mass when compacted into the cavities of the implant device.

In some embodiments, the composite interbody bone implant may comprise an allograft portion that is configured to be joined to another allograft portion or a non-allograft portion comprising a polymer. In this way, the composite interbody device can be joined before it is implanted at or near the target site. The composite interbody implant can have mating surfaces comprising recesses and/or projections and reciprocating recesses and/or projections (for example, joints) that allow the implant to be assembled before implantation. Assembly can also include, for example, use of an adhesive material to join parts of the implant together and provide strong interlocking fit.

The adhesive material may comprise polymers having hydroxyl, carboxyl, and/or amine groups. In some embodiments, polymers having hydroxyl groups include synthetic polysaccharides, such as for example, cellulose derivatives, such as cellulose ethers (for example, hydroxypropylcellulose). In some embodiments, the synthetic polymers having a carboxyl group, may comprise poly(acrylic acid), poly(meth-acrylic acid), poly(vinyl pyrrolidone acrylic acid-N-hydroxysuccinimide), and poly(vinyl pyrrolidone-acrylic acid-acrylic acid-N-hydroxysuccinimide) terpolymer. For example, poly(acrylic acid) with a molecular weight greater than 250,000 or 500,000 may exhibit particularly good adhesive performance. In some embodiments, the adhesive can be a polymer having a molecular weight of about 2,000 to about 5,000, or about 10,000 to about 20,000 or about 30,000 to about 40,000.

In some embodiments, the adhesive can comprise imido ester, p-nitrophenyl carbonate, N-hydroxysuccinimide ester, epoxide, isocyanate, acrylate, vinyl sulfone, orthopyridyl-disulfide, maleimide, aldehyde, iodoacetamide or a combination thereof. In some embodiments, the adhesive material can comprise at least one of fibrin, a cyanoacrylate (for example, N-butyl-2-cyanoacrylate, 2-octyl-cyanoacrylate), a collagen-based component, a glutaraldehyde glue, a hydrogel, gelatin, an albumin solder, and/or a chitosan adhesives. In some embodiments, the hydrogel comprises acetoacetate esters crosslinked with amino groups or polyethers as mentioned in U.S. Pat. No. 4,708,821. In some embodiments, the adhesive material can comprise poly(hydroxylic) compounds derivatized with acetoacetate groups and/or polyamino compounds derivatized with acetoacetamide groups by themselves or the combination of these compounds crosslinked with an amino-functional crosslinking compounds.

The adhesive can be a solvent based adhesive, a polymer dispersion adhesive, a contact adhesive, a pressure sensitive adhesive, a reactive adhesive, such as for example multi-part adhesives, one part adhesives, heat curing adhesives, moisture curing adhesives, or a combination thereof or the like. The adhesive can be natural or synthetic or a combination thereof.

Contact adhesives are used in strong bonds with high shear-resistance. Pressure sensitive adhesives form a bond by the application of light pressure to bind the adhesive with the target tissue site, cannula and/or expandable member. In some embodiments, to have the device adhere to the target tissue site, pressure is applied in a direction substantially perpendicular to a surgical incision.

Multi-component adhesives harden by mixing two or more components, which chemically react. This reaction causes polymers to cross-link into acrylics, urethanes, and/or epoxies. There are several commercial combinations of multi-component adhesives in use in industry. Some of these combinations are: polyester resin-polyurethane resin; polyols-polyurethane resin, acrylic polymers-polyurethane resins or the like. The multi-component resins can be either solvent-based or solvent-less. In some embodiments, the solvents present in the adhesives are a medium for the polyester or the polyurethane resin. Then the solvent is dried during the curing process.

In some embodiments, the adhesive can be a one-part adhesive. One-part adhesives harden via a chemical reaction with an external energy source, such as radiation, heat, and moisture. Ultraviolet (UV) light curing adhesives, also known as light curing materials (LCM), have become popular within the manufacturing sector due to their rapid curing time and strong bond strength. Light curing adhesives are generally acrylic based. The adhesive can be a heat-curing adhesive, where when heat is applied (for example, body heat), the components react and cross-link. This type of adhesive includes epoxies, urethanes, and/or polyimides. The adhesive can be a moisture curing adhesive that cures when it reacts with moisture present (for example, bodily fluid) on the substrate surface or in the air. This type of adhesive includes cyanoacrylates or urethanes. The adhesive can have natural components, such as for example, vegetable matter, starch (dextrin), natural resins or from animals for example casein or animal glue. The adhesive can have synthetic components based on elastomers, thermoplastics, emulsions, and/or thermosets including epoxy, polyurethane, cyanoacrylate, or acrylic polymers.

In some embodiments, the interbody bone implant may be joined together utilizing pins, rods, clips, or other fasteners to allow strong and easily coupling of component parts. In some embodiments, the allograft material is configured to provide the most contact to tissue surfaces (for example, the allograft material can be on the perimeter of the device, while the polymer material is situated in the interior of the device.

In one embodiment, the osteoinductive material comprises allograft tissue. Non-limiting examples of a bone graft material include demineralized bone matrix, or a bone composite. While allograft bone is a desirable alternative to autograft, it must be rigorously processed and terminally sterilized prior to implantation to remove the risk of disease transmission or an immunological response. This processing removes the osteogenic and osteoinductive properties of the allograft, leaving only an osteoconductive scaffold. These scaffolds are available in a range of preparations (such as morselized particles and struts) for different orthopedic applications.

In one embodiment, to improve the osteoinductive properties, it is desirable to use demineralized bone matrix (DBM) as the osteoinductive material, due to its superior biological properties relative to undemineralised allograft bone, since the removal of minerals increases the osteoinductivity of the graft. Currently, there are a range of DBM products in clinical use.

Demineralized bone matrix (DBM) is demineralized allograft bone having osteoinductive activity. DBM is prepared by acid extraction of allograft bone, resulting in loss of most of the mineralized component but retention of collagen and noncollagenous proteins, including growth factors. DBM does not contain osteoprogenitor cells, but the efficacy of a demineralized bone matrix as a bone-graft substitute or extender may be influenced by a number of factors, including the sterilization process, the carrier, the total amount of bone morphogenetic protein (BMP) present, and the ratios of the different BMPs present. DBM includes demineralized pieces of cortical bone to expose the osteoinductive proteins contained in the matrix. These activated demineralized bone particles are usually added to a substrate or carrier (for example glycerol or a polymer). DBM is mostly an osteoinductive product, but lacks enough induction to be used on its own in challenging healing environments such as posterolateral spine fusion.

According to some embodiments of the disclosure, the demineralized bone matrix may comprise demineralized bone matrix fibers and/or demineralized bone matrix chips. In some embodiments, the demineralized bone matrix may comprise demineralized bone matrix fibers and demineralized bone matrix chips in a 30:60 ratio. In some embodiments, the bone allograft material comprises demineralized bone matrix fibers and demineralized bone matrix chips in a ratio of 25:75 to about 75:25 fibers to chips.

According to one embodiment of the disclosure, the bone composite comprises a bone powder, a polymer and a demineralized bone. In different embodiments of the disclosure, bone powder content can range from about 5% to about 90% w/w, polymer content can range from about 5% to about 90% w/w, and demineralized bone particles content comprises the reminder of the composition. In various embodiments, the demineralized bone particles comprise from about 20% to about 40% w/w while the polymer and the bone powder comprise each from about 20% to about 60% w/w of the composition. The bone graft materials of the present disclosure include those structures that have been modified in such a way that the original chemical forces naturally present have been altered to attract and bind molecules, including, without limitation, growth factors and/or cells, including cultured cells.

Namely, the demineralized allograft bone material may be further modified such that the original chemical forces naturally present have been altered to attract and bind growth factors, other proteins and cells affecting osteogenesis, osteoconduction and osteoinduction. For example, a demineralized allograft bone material may be modified to provide an ionic gradient to produce a modified demineralized allograft bone material, such that implanting the modified demineralized allograft bone material results in enhanced ingrowth of host bone.

In one embodiment an ionic force change agent may be applied to modify the demineralized allograft bone material. The demineralized allograft bone material may comprise, for example, a demineralized bone matrix (DBM) comprising fibers, particles and any combination of thereof. According to another embodiment, a bone graft structure may be used which comprises a composite bone, which includes a bone powder, a polymer and a demineralized bone.

The ionic force change agent may be applied to the entire demineralized allograft bone material or to selected portions/surfaces thereof. The ionic force change agent may be a binding agent, which modifies the demineralized allograft bone material or bone graft structure to bind molecules, such as, for example, growth factors, or cells, such as, for example, cultured cells, or a combination of molecules and cells. In the practice of the disclosure the growth factors include but are not limited to BMP-2, rhBMP-2, BMP-4, rhBMP-4, BMP-6, rhBMP-6, BMP-7(OP-1), rhBMP-7, GDF-5, LIM mineralization protein, platelet derived growth factor (PDGF), transforming growth factor-$\beta$ (TGF-$\beta$), insulin-related growth factor-I (IGF-I), insulin-related growth factor-II (IGF-II), fibroblast growth factor (FGF), beta-2-microglobulin (BDGF II), and rhGDF-5. A person of ordinary skill in the art will appreciate that the disclosure is not limited to growth factors only. Other molecules can also be employed in the disclosure. For example, tartrate-resistant acid phosphatase, which is not a growth factor, may also be used in the disclosure.

If a cell culture is employed, the cells include but are not limited to mesenchymal stems cells, pluripotent stem cells, osteoprogenitor cells, osteoblasts, osteoclasts, and any bone marrow-derived cell lines.

In some embodiments, the ionic force change agent comprises at least one of enzymes, enzyme mixtures, pressure (for example, isostatic pressure), chemicals, heat, sheer force, oxygen plasma, or a combination thereof. For example, the ionic force change agent may comprise an enzyme such as collagenase or pepsin, which can be administered for a sufficient period of time to partially digest at least a portion of the demineralized allograft bone material. Subsequently, the enzyme may be deactivated and/or removed.

Any enzyme or enzyme mixture may be contemplated, and treatment time durations may be altered in accordance with the enzyme(s) used. Some suitable enzymes that may degrade the DBM material include, but are not limited to, cysteine proteinases, matrix metalloproteinases, enzymes such as amylases, proteases, lipases, pectinases, cellulases, hemicellulases, pentosanases, xylanases, phytases or combinations thereof. Exemplary enzymes suitable to partially degrade and modify the DBM material, include but are not limited to, cathepsin L, cathepsin K, cathepsin B, collagenase, pepsin, plasminogen, elastase, stromelysin, plasminogen activators, or a combination thereof.

In some embodiments, the DBM material can be subjected to pressure to modify it. The simplest pressing technique is to apply pressure to the unconstrained DBM material. Examples include pressing the DBM material using a mortar and pestle, applying a rolling/pressing motion such as is generated by a rolling pin, or pressing the bone pieces between flat or curved plates. These flattening pressures cause the DBM material fibers to remain intact.

Another pressing technique involves mechanically pressing demineralized bone material, which can be constrained within a sealed chamber having a hole (or a small number of holes) in its floor or bottom plate. The separated fibers extrude through the holes with the hole diameter limiting the maximum diameter of the extruded fibers. This constrained technique results in fibers that are largely intact (as far as length is concerned).

In a combined unconstrained/constrained pressing technique that results in longer fibers by minimizing fiber breakage, the demineralized bone is first pressed into an initially separated mass of fibers while in the unconstrained condition and thereafter these fibers are constrained within the sealed chamber where pressing is continued.

In general, pressing of demineralized bone to provide demineralized bone particles can be carried out at from about 1,000 to about 40,000 psi, and, in certain embodiments, at from about 5,000 to about 20,000 psi.

Subsequent to the addition of the ionic force change agent, the practitioner may optionally administer an appropriate molecule or cell culture. Generally, the molecule or cell culture is applied within minutes, for example from about 1 to about 120 minutes before implantation into the patient.

One class of molecules suitable for one embodiment of the disclosure is growth factors. Growth factors suitable for use in the practice of the disclosure include but are not limited to bone morphogenic proteins, for example, BMP-2, rhBMP-2, BMP-4, rhBMP-4, BMP-6, rhBMP-6, BMP-7 (OP-1), rhBMP-7, GDF-5, and rhGDF-5. Bone morphogenic proteins have been shown to be excellent at growing bone and there are several products being tested. For example, rhBMP-2 delivered on an absorbable collagen sponge (INFUSE® Bone Graft, Medtronic Sofamor Danek, Memphis, Tenn.) has been used inside titanium fusion cages and resulted in successful fusion and can be used on a ceramic carrier to enhance bone growth in a posterolateral fusion procedure. rhBMP-2 can also be used on a carrier for acute, open fractures of the tibial shaft. BMP-7 (OP-1) also enhances bone growth in a posterolateral fusion procedure.

Additionally, suitable growth factors include, without limitation, LIM mineralization protein, platelet derived growth factor (PDGF), transforming growth factor β (TGF-β), insulin-related growth factor-I (IGF-I), insulin-related growth factor-II (IGF-II), fibroblast growth factor (FGF), and beta-2-microglobulin (BDGF II).

Further, molecules, which do not have growth factor properties may also be suitable for this disclosure. An example of such molecules is tartrate-resistant acid phosphatase.

In one embodiment, the demineralized allograft bone material is treated with a negatively-charged ionic force change agent to produce a negatively-charged demineralized allograft bone material. The negatively-charged demineralized allograft bone material attracts a positively charged molecule having a pI from about 8 to about 10. Examples of positively charged molecules having a pI from about 8 to about 10 include but are not limited to, rhBMP-2 and rhBMP-6.

In another embodiment, the demineralized allograft bone material is treated with a positively-charged ionic force change agent such that the positively-charged demineralized allograft bone material attracts a molecule with a slightly negative charge, for example a charge of pI about 5 to about 7. Examples of molecules having a slightly negative charge include rhBMP-4.

In yet another embodiment, the demineralized allograft bone material is treated with a positively-charged ionic force change agent to produce a positively-charged demineralized allograft bone material such that cells, in particular cell cultures having a negative surface charge bind to the positively-charged demineralized allograft bone material. Examples of cells which are suitable for use in the practice of the disclosure include but are not limited to mesenchymal stems cells, pluripotent stem cells, embryonic stem cells, osteoprogenitor cells and osteoblasts.

The mechanisms by which a demineralized allograft bone material may acquire ionic forces include but are not limited to ionization, ion adsorption and ion dissolution. In one embodiment, the implant is modified to give it the selected charge by a one-to-one substitution of the calcium ion with lithium, sodium, potassium or cesium of hydroxyapatite.

In yet another aspect, treatments with gradient-affecting elements, such as elements present in hydroxyapatite, and human proteins are employed. Suitable gradient-affecting proteins are those present in the organic phase of human bone tissue. The gradient-affecting proteins derive molecule or cell attraction without the potential damaging effects on the implants, as may be the case with other chemical treatments. Usually this is accomplished through surface treatments such as, for example, plasma treatment to apply an electrostatic charge on bone.

The term "plasma" in this context is an ionized gas containing excited species such as ions, radicals, electrons and photons. The term "plasma treatment" refers to a protocol in which a surface is modified using a plasma generated from process gases including, but not limited to, $O_2$, He, $N_2$, Ar and $N_2O$. To excite the plasma, energy is applied to the system through electrodes. This power may be alternating current (AC), direct current (DC), radiofrequency (RF), or microwave frequency (MW). The plasma may be generated in a vacuum or at atmospheric pressure. The plasma can also be used to deposit polymeric, ceramic or metallic thin films onto surfaces. Plasma treatment is an effective method to uniformly alter the surface properties of substrates having different or unique size, shape and geometry including but not limited to bone and bone composite materials.

In some embodiments, the implant device of the present disclosure having osteoinductive material retained therein may be used to provide temporary or permanent fixation along an orthopedic target site. For example, the expandable implant device may be introduced into an intervertebral disc space while secured to a surgical insertion instrument and thereafter manipulated into the proper orientation before being released. According to one aspect, the implant device may be introduced into a target site through use of any of a variety of suitable surgical instruments having the capability to engage the implant device. For example, a clinician may utilize the implant in a minimally invasive spinal fusion procedure. After creation of a working channel and preparation of the disc space, a single implant device may be grasped and placed into the intervertebral disc space. Additional materials and tools may be included in the procedure before, during, or after the insertion of the implant to aid in introducing the implant into a targeted spinal site.

In some embodiments, the substance may be designed to expand in vivo. Such an embodiment may be used to fill a space and create contact with congruent surfaces as it expands in vivo, for example for interbody fusion. Thus, in some embodiments, the implant device may be used in the disc space, between implants, or inside a cage.

In some embodiments, the implant devices described in this disclosure can expand when they come in contact with water or other bodily fluids, either by way of liquid absorption, or by stretching the component materials of these implant devices. As described above, the substances from which the implant devices are made can include a natural and/or synthetic expandable material. For example, when the implant devices are made from allograft, then the allograft expands when it comes into contact with bodily fluids. Similarly, when the implant devices include a polymer skeleton having cavities, the cavities can be filled with expandable material which results in expanding the implant devices when they come into contact with bodily fluids. As described above, expandable material useful to fill up skeleton cavities can comprise bone particles, a polymer, a hydrogel, a sponge, collagen, or other material. In various embodiments, the expandable material comprises bone allograft comprising demineralized bone particles, and the demineralized bone particles may be a blend of cortical and cancellous bone. For example, the expandable material can comprise demineralized cortical fibers and demineralized cancellous chips, wherein the demineralized cancellous chips can create a matrix for the incorporation of new bone and add advanced expansion characteristics.

In addition to bone particles, an expandable polymer, a collagen sponge, compressed and/or dried hydrogels, or other materials may be used. In addition to expansion properties, the material may exhibit osteoinductive and/or osteoconductive properties. For example, cancellous bone particles may exhibit osteoconductive properties while demineralized cortical bone particles may exhibit osteoinductive properties.

The expandable material may be compressed during formation to aid in subsequent expansion. Generally, increased compression leads to increased expansion characteristics in the osteoimplant. Compressed materials and certain non-compressed materials may be constrained such that, absent the constraint, the material is free to expand. A constrained material is one that embodies energy, such as a bent, spring-loaded, or coiled material, or any other material that is artificially prevented from expanding or conforming to its natural configuration. The expandable material can be included as filler in skeleton cavities that partially or wholly surround the material.

Expansion may be activated in any suitable manner. For example, expansion may be activated by exposure of the implant device to air, water, blood, heat, removal of a constraint, or otherwise. In one embodiment, the expandable material may be provided compressed and dried. Upon exposure to liquid in vivo, the expandable material may expand. In another embodiment, the expandable may be compressed in the skeleton cavities or at least partially constrained in the skeleton cavities. Upon exposure to liquid in vivo, the cavity filling material may expand or disintegrate, as the expandable material expands. The expandable material may expand as a function of time. In yet another embodiment, the expandable material may have a first state at approximately 60° F. and an expanded state at approximately 98° F. such that, upon implantation in vivo and exposure to body heat, the expandable material may expand. In a further embodiment, the expandable material may be vacuum-sealed during manufacture and, when unsealed and exposed to air, the expandable material may expand.

Having been deposited in the disc space, an implant device of the present disclosure effects spinal fusion over time as the natural healing process integrates and binds the implant within the intervertebral space by allowing a boney bridge to form through the implant and between the adjacent vertebral bodies.

In some embodiments, an implant device of the present disclosure may be used to deliver substances such as surface demineralized bone chips, optionally of a predetermined particle size, demineralized bone fibers, optionally pressed, and/or allograft.

For embodiments where the substance is biologic, the substance may be autogenic, allogenic, xenogenic, or transgenic. However, it is contemplated that other suitable materials may be positioned in the implant device such as, for example, protein, nucleic acid, carbohydrate, lipids, collagen, allograft bone, autograft bone, cartilage stimulating substances, allograft cartilage, TCP, hydroxyapatite, calcium sulfate, polymer, nanofibrous polymers, growth factors, carriers for growth factors, growth factor extracts of tissues, demineralized bone matrix, dentine, bone marrow aspirate, bone marrow aspirate combined with various osteoinductive or osteoconductive carriers, concentrates of lipid derived or marrow derived adult stem cells, umbilical cord derived stem cells, adult or embryonic stem cells combined with various osteoinductive or osteoconductive carriers, transfected cell lines, bone forming cells derived from periosteum, combinations of bone stimulating and cartilage stimulating materials, committed or partially committed cells from the osteogenic or chondrogenic lineage, or combinations of any of the above. In some embodiments, the substance may be pressed before placement in the implant device. A substance provided within the implant device may be homogenous, or generally a single substance, or may be heterogeneous, or a mixture of substances.

In some embodiments the substance delivered by the implant device may include or comprise an additive such as an angiogenesis promoting material or a bioactive agent. It will be appreciated that the amount of additive used may vary depending upon the type of additive, the specific activity of the particular additive preparation employed, and the intended use of the composition. The desired amount is readily determinable by one skilled in the art. Angiogenesis may be an important contributing factor for the replacement of new bone and cartilage tissues. In certain embodiments, angiogenesis is promoted so that blood vessels are formed at an implant site to allow efficient transport of oxygen and other nutrients and growth factors to the developing bone or cartilage tissue. Thus, angiogenesis promoting factors may be added to the substance to increase angiogenesis. For example, class 3 semaphorins, for example, SEMA3, controls vascular morphogenesis by inhibiting integrin function in the vascular system, and may be included in the recovered hydroxyapatite.

In accordance with some embodiments, the substance may be supplemented, further treated, or chemically modified with one or more bioactive agents or bioactive compounds. Bioactive agent or bioactive compound, as used herein, refers to a compound or entity that alters, inhibits, activates, or otherwise affects biological or chemical events. For example, bioactive agents may include, but are not limited to, osteogenic or chondrogenic proteins or peptides; demineralized bone powder; collagen, insoluble collagen derivatives, and soluble solids and/or liquids dissolved therein; anti-AIDS substances; anti-cancer substances; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anti-cholinergics; anti-glaucoma compounds; anti-parasite and/or anti-protozoal compounds; modulators of cell-extracellular matrix interactions including cell growth inhibitors and antiadhesion molecules; vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anticoagulants and/or antithrombotic agents; local anesthetics; ophthalmics; prostaglandins; anti-depressants; anti-psychotic substances; anti-emetics; imaging agents; biocidal/biostatic sugars such as dextran, glucose; amino acids; peptides; vitamins; inorganic elements; co-factors for protein synthesis; endocrine tissue or tissue fragments; synthesizers; enzymes such as alkaline phosphatase, collagenase, peptidases, oxidases; polymer cell scaffolds with parenchymal cells; collagen lattices; antigenic agents; cytoskeletal agents; cartilage fragments; living cells such as chondrocytes, bone marrow cells, mesenchymal stem cells; natural extracts; genetically engineered living cells or otherwise modified living cells; expanded or cultured cells; DNA delivered by plasmid, viral vectors, or other means; tissue transplants; autogenous tissues such as blood, serum, soft tissue, bone marrow; bioadhesives; bone morphogenic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, for example, interleukin-1 (IL-1), interleukin-2 (IL-2); human alpha thrombin; transforming growth factor (TGF-β); insulin-like growth factors (IGF-1, IGF-2); parathyroid hormone (PTH); platelet derived growth factors (PDGF); fibroblast growth factors (FGF, BFGF); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, for example, fatty acid esters such as laureate, myristate and stearate monoesters of polyethylene glycol, enamine derivatives, alpha-keto aldehydes; and nucleic acids or combinations thereof.

In certain embodiments, the bioactive agent may be a drug. In some embodiments, the bioactive agent may be a growth factor, cytokine, extracellular matrix molecule, or a fragment or derivative thereof, for example, a protein or peptide sequence such as RGD.

In one embodiment of an implant device comprising at least one cavity, it may be contemplated that any combination or mixture of same or different substances may be placed and retained therein, and further, different substances may be placed within the same or different cavities.

Sterilization

A medical implant device according to the present disclosure including its contents may be sterilizable. In various embodiments, one or more components of the implant device and/or its contents are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

In various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the medical device has gel components.

Other methods may also be used to sterilize the device and/or one or more components of the device and/or contents, including, but not limited to, gas sterilization, such as, for example, with ethylene oxide or steam sterilization.

Method of Use

An implant device according to the present disclosure delivers the substance or substances in vivo. Active delivery of the substance may include the cleavage of physical and/or chemical interactions of substance from covering with the presence of body fluids, extracellular matrix molecules, enzymes or cells. Further, it may comprise formation change of substances (growth factors, proteins, polypeptides) by body fluids, extracellular matrix molecules, enzymes or cells.

The body of the implant device is loaded with the substance for placement in vivo. The body may be pre-loaded, thus loaded at manufacture, or may be loaded in the operating room or at the surgical site. Preloading may be done with any of the substances previously discussed including, for example, allograft such as DBM, synthetic calcium phosphates, synthetic calcium sulfates, enhanced DBM, collagen, carrier for stem cells, and expanded cells (stem cells or transgenic cells). Loading in the operating room or at the surgical site may be done with any of these materials and further with autograft and/or bone marrow aspirate.

Any suitable method may be used for loading a substance in the implant device in the operating room or at the surgical site. For example, the substance may be spooned into the cavity(ies) of the implant device, the substance may be placed in the implant device using forceps, the substance may be loaded into the implant device using a syringe (with or without a needle), or the substance may be inserted into the implant device in any other suitable manner. Specific embodiments for loading at the surgical site include for example, vertebroplasty or interbody space filler.

For placement, the substance or substances may be provided in the implant device and the implant device placed in vivo. In one embodiment, the implant device is placed in vivo by placing the implant device in a catheter or tubular inserter and delivering the implant device with the catheter or tubular inserter. The implant device, with a substance provided therein, may be steerable such that it can be used with flexible introducer instruments for, for example, minimally invasive spinal procedures. For example, the implant device may be introduced down a tubular retractor or scope, during XLIF, TLIF, or other procedures. In other embodiments, the implant device (with or without substance loaded) may be placed in a cage, for example, for interbody fusion. Attachment mechanisms provided on the implant device may be used to couple the device to a site in vivo.

Applications

An implant device according to the present disclosure may be configured for use in any suitable application. In some embodiments, the implant device may be used in healing vertebral compression fractures, interbody fusion, minimally invasive procedures, posterolateral fusion, correction of adult or pediatric scoliosis, treating long bone defects, osteochondral defects, ridge augmentation (dental/craniomaxillofacial, for example edentulous patients), beneath trauma plates, tibial plateau defects, filling bone cysts, wound healing, around trauma, contouring (cosmetic/plastic/reconstructive surgery), and others. The implant device may be used in a minimally invasive procedure via placement through a small incision, via delivery through a tube, or other. The size and shape of the device may advantageously be designed in accordance with restrictions on delivery conditions.

An exemplary application for using an implant device as disclosed is fusion of the spine. In clinical use, the implant device and delivered substance may be used to bridge the gap between the transverse processes of adjacent or sequential vertebral bodies. The implant device may be used to bridge two or more spinal motion segments. The implant device surrounds the substance to be implanted, and contains the substance to provide a focus for healing activity in the body. In other applications, the implant device may be applied to transverse processes or spinous processes of vertebrae.

Generally, the implant device may be applied to a preexisting defect, to a created channel, or to a modified defect. Thus, for example, a channel may be formed in a bone, or a pre-existing defect may be cut to form a channel, for receipt of the implant device. The implant device may be configured to match the channel or defect. In some embodiments, the configuration of the implant device may be chosen to match the channel. In other embodiments, the channel may be created, or the defect expanded or altered, to reflect a configuration of the implant device. The implant device may be placed in the defect or channel and, optionally, coupled using attachment mechanisms.

At the time just prior to when the implant device is to be placed in a defect site, optional materials, for example, autograft bone marrow aspirate, autograft bone, preparations of selected autograft cells, autograft cells containing genes encoding bone promoting action, can be combined with the implant device and/or with a substance provided in the implant device. The implant device can be implanted at the bone repair site, if desired, using any suitable affixation means, for example, sutures, staples, bioadhesives, screws, pins, rivets, other fasteners and the like or it may be retained in place by the closing of the soft tissues around it.

Although the disclosure has been described with reference to some embodiments, persons skilled in the art will recognize that changes may be made in form and detail without departing from the spirit and scope of the disclosure.

What is claimed is:

1. An expandable implant device for implantation at a surgical site, the implant device comprising: a top piece and a bottom piece, the bottom piece comprising bone material insertable into a disc space, the bottom piece having superior and inferior surfaces and a longitudinal axis, said bottom piece configured to couple with the top piece comprising cortical bone and having superior and inferior surfaces and a longitudinal axis, the bottom piece having a flat leading end face perpendicular to the longitudinal axis of the bottom piece and the superior surface of the bottom piece having a ramped portion extending at an incline relative to the longitudinal axis of the bottom piece and a non-ramped portion extending parallel to said longitudinal axis, the ramped portion extending only partially along the length of the superior surface such that the leading end face of the bottom piece comprises a greater height than an opposite end face of the bottom piece, the top piece having a leading bullet-shaped end, the leading bullet-shaped end of the top piece configured to distract open an intervertebral disc space by slidably inserting the top piece over the bottom piece, the inferior surface of the top piece having a ramped portion such that the leading end of the top piece comprises a lesser height than an opposite end of the top piece, the implant device is configured to contact host bone and the implant device comprises non-bone material, a contact surface area of the non-bone material and the cortical bone to the host bone comprising from about 5% to about 50% of the implant, wherein the superior surface of the bottom piece comprises a first pair of angled surfaces extending from the superior surface, the first pair of angled surfaces forming a triangular valley extending longitudinally along the superior surface and the inferior surface of the top piece comprises a second pair of angled surfaces extending from the inferior surface, the second pair of angled surfaces forming a triangular peak extending longitudinally along the inferior surface, the triangular valley and triangular peak configured to interlock with each other.

2. An expandable implant device of claim 1, wherein (i) the implant device comprises surface demineralized cortical bone, (ii) the contact surface area of the non-bone material and the cortical bone to the host bone comprising from about 10% to about 20% of the implant device; (iii) the implant device comprises non-bone material and the non-bone material comprises from about 10 wt. % to about 60 wt. % of implant device or (iv) the implant device comprises bone material and the bone material comprises from about 40 wt. % to about 90 wt. % of the implant device.

3. An expandable implant device of claim 1, further comprising a recess, projection, rib, groove or a combination thereof.

4. An expandable implant device of claim 1, wherein the bottom piece and the top piece have a shape comprising circular, oblong, oval, curved, triangular, other polygonal or non-polygonal shapes.

5. An expandable implant device of claim 1, wherein the implant device further comprises a synthetic polymer.

6. An expandable implant device of claim 1, wherein the implant device includes a uniform height when the top piece is coupled with the bottom piece.

7. An expandable implant device for implantation at a surgical site, the implant device comprising: a top piece and a bottom piece, the bottom piece having non-bone material and comprising at least one cavity, the bottom piece configured for insertion into a disc space, the bottom piece having superior and inferior surfaces and a longitudinal axis configured to couple with the top piece of non-bone material including at least one cavity, the bottom piece having a flat leading end face perpendicular to the longitudinal axis of the bottom piece and the superior surface of the bottom piece having a ramped portion extending at an incline relative to the longitudinal axis of the bottom piece and a non-ramped portion extending parallel to said longitudinal axis, the ramped portion extending only partially along the length of the superior surface such that the leading end face of the bottom piece comprises a greater height than an opposite end face of the bottom piece, the top piece having superior and inferior surfaces and a bullet-shaped leading end and a trailing end and a longitudinal axis, the leading bullet-shaped end of the top piece configured to distract open an intervertebral disc space by slidably inserting the top piece over the bottom piece, the inferior surface of the top piece having a ramped portion such that the leading end of the top piece comprises a lesser height than the trailing end of the top piece, the implant device is configured to contact host bone, a contact surface area of the non-bone material and to the host bone comprising from about 5% to about 50% of the implant, wherein the superior surface of the bottom piece comprises a first pair of angled surfaces extending from the superior surface, the first pair of angled surfaces forming a triangular valley extending longitudinally along the superior surface and the inferior surface of the top piece comprises a second pair of angled surfaces extending from the inferior surface, the second pair of angled surfaces forming a triangular peak extending longitudinally along the inferior surface, the triangular valley and triangular peak configured to interlock with each other.

8. An expandable implant device of claim 7, wherein a first bone allograft material is configured to fit within the at least one cavity of the top piece and/or a second bone allograft material is configured to fit within the at least one cavity of the bottom piece.

9. An expandable implant device of claim 8, wherein one of the first bone allograft material or the second bone allograft material comprises demineralized bone matrix.

10. An expandable implant device of claim 9, wherein one of the first bone allograft material or the second bone allograft material comprises demineralized bone matrix fibers and demineralized bone matrix chips in a ratio of 25:75 to about 75:25 fibers to chips.

11. An expandable implant device of claim 7, wherein the non-bone material includes at least one of a polymer, ceramic, metal or combinations thereof.

12. An expandable implant device of claim 11, wherein the polymer comprises poly-ether-ether-ketone (PEEK), poly-ether-ketone-ketone (PEKK), or a combination thereof.

13. An expandable implant device of claim 7, wherein a biocompatible material is disposed within the at least one cavity of the top piece and/or the bottom piece.

14. An expandable implant device of claim 13, wherein the biocompatible material comprises at least one of autologous bone, a ceramic bone void filler, bone allograft, bone xenograft, cortical bone, a growth factor, a non-bone implant material, or a combination thereof.

15. An expandable implant device of claim 7, wherein the superior surface of the bottom piece and the inferior surface of the top piece comprise a recess, projection, rib, groove, or a combination thereof configured to interlock the bottom piece with the top piece.

* * * * *